United States Patent
Mitsunaga et al.

(10) Patent No.: US 9,086,367 B2
(45) Date of Patent: Jul. 21, 2015

(54) X-RAY INTENSITY CORRECTION METHOD AND X-RAY DIFFRACTOMETER

(71) Applicant: Rigaku Corporation, Akishima-shi, Tokyo (JP)

(72) Inventors: Toru Mitsunaga, Hachioji (JP); Kazuhiko Omote, Akiruno (JP); Katsuhiko Inaba, Yokohama (JP)

(73) Assignee: RIGAKU CORPORATION, Tokyo (JP)

( * ) Notice: Subject to any disclaimer, the term of this patent is extended or adjusted under 35 U.S.C. 154(b) by 202 days.

(21) Appl. No.: 13/662,082

(22) Filed: Oct. 26, 2012

(65) Prior Publication Data

US 2013/0121460 A1    May 16, 2013

(30) Foreign Application Priority Data

Nov. 11, 2011  (JP) ................................ 2011-247327
Mar. 2, 2012   (JP) ................................ 2012-047247

(51) Int. Cl.
  *G01N 23/207* (2006.01)
  *G01N 23/223* (2006.01)
  *G01N 23/20*  (2006.01)

(52) U.S. Cl.
  CPC ........ *G01N 23/207* (2013.01); *G01N 23/20008* (2013.01); *G01N 23/223* (2013.01)

(58) Field of Classification Search
  CPC ............ G01N 23/207; G01N 23/2206; G01N 23/20008; G01N 23/223; G01N 2223/056; G01N 2223/076
  USPC ............................................................ 378/44
  See application file for complete search history.

(56) References Cited

U.S. PATENT DOCUMENTS

| | | | | |
|---|---|---|---|---|
| 5,373,544 A * | 12/1994 | Goebel | ........................... | 378/71 |
| 7,149,279 B2 | 12/2006 | Kumakhov | | |
| 2005/0041776 A1* | 2/2005 | Kumakhov et al. | ............. | 378/71 |

FOREIGN PATENT DOCUMENTS

| | | |
|---|---|---|
| GB | 774572 A | 5/1957 |
| JP | 2007-17258 A | 1/2007 |

* cited by examiner

*Primary Examiner* — Glen Kao
*Assistant Examiner* — Dani Fox
(74) *Attorney, Agent, or Firm* — Birch, Stewart, Kolasch & Birch, LLP

(57) ABSTRACT

An X-ray intensity correction method makes the background uniform by adjusting a raster element and an X-ray diffractometer. An X-ray intensity correction method for correcting the intensity of diffracted X-rays includes the steps of focusing X-rays on a sample for correction placed at a gonio center, entering fluorescent X-rays excited by the focused X-rays into a raster element formed by polycapillaries and having a unique focal point, detecting the fluorescent X-rays having passed through the raster element; and adjusting the arrangement of the raster element so that the fluorescent X-rays can uniformly be detected regardless of the detecting position. Since fluorescent X-rays are used, it is possible to adjust the position of the raster element because if the focal point of the raster element coincides with the gonio center, the intensity becomes uniform regardless of the detected position.

10 Claims, 19 Drawing Sheets

X-RAY INTENSITY CORRECTION METHOD AND X-RAY DIFFRACTOMETER

FIELD OF THE INVENTION

The present invention relates to an X-ray intensity correction method for correcting the intensity of diffracted X-rays by making the background uniform, and an X-ray diffractometer.

DESCRIPTION OF RELATED ART

Conventionally, the Kumakhovlens is known, which is capable of focusing X-rays emitted in a wide range. The Kumakhov lens has a honeycomb structure in which polycapillaries are integrated and is manufactured by repeatedly bundling and stretching glass tubes, and has a number of minute and parallel holes open therein. When X-rays are incident on such a minute hole, X-rays incident at a small angle are totally reflected and pass therethrough, but others are absorbed by a wall. By utilizing this, it is possible to configure a lens by bending the trajectory of X-ray along the capillary.

Furthermore, by cutting out a part of the glass polycapillary as described above, bending at a desired curvature, and being processed into the shape of a sphere, it is also possible to utilize the glass polycapillary as a collimator in which countless numbers of minute holes parallel to the radial direction with respect to a predetermined center are open. Such a collimator is referred to as a raster element and there is known a diffracted X-ray measurement method using the raster element. FIG. 18 is a perspective view showing a configuration of a general raster element.

For example, the detecting unit for X-ray diffraction measurements described in the specification of U.S. Pat. No. 7,149,279 includes the collimating system installed in front of the detector. In addition, the collimating system has a honeycomb structure of bent polycapillaries and has a mechanism capable of adjusting the position thereof with respect to the detection surface of the detector. The position adjusting mechanism of this collimating system is configured to adjust the selective passing of X-rays (see from the 45th to 61st lines on the 7th section).

However, when intending to detect diffracted X-rays through the use of the detecting unit as described above, if the adjustment of arrangement of the raster element is insufficient, the ratio of incident X-rays absorbed by the capillary of the raster element increases depending on the detected position, and thus the intensity of X-ray detected in that position is reduced. As a result, when diffracted X-rays are detected, the intensity of the background becomes non-uniform and there may be caused a case where it is not possible to obtain necessary information from the diffracted rays.

FIG. 19 is a graph showing the intensities of the background by fluorescent X-rays from a sample by the detection method with and without the raster element, respectively. As shown in FIG. 19, when data is acquired with the detector fixed without the raster element, it is possible to detect data of the uniform background. In contrast, when the intensity of the background having passed through the raster element is measured, the intensity is reduced in the position on the side of higher angles in comparison with that on the side of lower angles.

Moreover, even in the conventional device, it is also possible to adjust the arrangement of the raster element, but even if adjustment is tried to be made so that the focal position of the element and the gonio center can be set at each other, the raster element is bent, and thus it is hard to recognize the focal position and to make adjustment.

BRIEF SUMMARY OF THE INVENTION

The present invention has been made in view of such circumstances and an object thereof is to provide an X-ray intensity correction method capable of easily adjusting a raster element and of making the background uniform at the time of measurement, and an X-ray diffractometer.

(1) In order to achieve the above-mentioned object, an X-ray intensity correction method of the present invention is an X-ray intensity correction method for correcting the intensity of diffracted X-rays by making the background uniform by fluorescent X-rays and characterized by including the steps of: focusing X-rays on a sample for correction placed at a gonio center, entering the fluorescent X-rays excited by the focused X-rays into a raster element formed by polycapillaries and having a unique focal point, and detecting the fluorescent X-rays having passed through the raster element, and adjusting the arrangement of the raster element so that the fluorescent X-rays can uniformly be detected regardless of the detecting position.

As described above, in the X-ray intensity correction method of the present invention, the fluorescent X-ray is used at the time of adjustment, and thus it is possible to enter the X-rays with which the spherical surface is uniformly irradiated by the gonio center, into the raster element. At this time, by utilizing the fact that if the focal point of the raster element coincides with the gonio center, the intensity of the detected X-rays is uniform regardless of the detected angle, it is possible to adjust the position of the raster element. Because of this, it is possible to easily adjust the raster element to an optimum position and to make the background uniform at the time of measurement.

(2) Furthermore, the X-ray intensity correction method of the present invention is characterized in that the arrangement of the raster element is adjusted until the minimum value become half or more of the maximum value on the intensity in the two-dimensional image obtained by the detected fluorescent X-rays. Because of this, it is possible to sufficiently adjust the arrangement of the raster element and to make the background uniform at the time of measurement. It should be noted that it is further preferable that the intensity in each position is within ±20% of the average intensity.

(3) In addition, the X-ray intensity correction method of the present invention is characterized in that the arrangement of the raster element is adjusted by moving the raster element in a translation direction and in a tilting direction in accordance with the intensity distribution of the image of the fluorescent X-rays having passed through the raster element. Because of this, it is known in which direction the movement of translation or tilting is necessary in accordance with the pattern of the intensity distribution, and thus it is possible to efficiently adjust the arrangement of the raster element.

(4) Moreover, the X-ray intensity correction method of the present invention is characterized by further including the step of entering the X-rays diffracted by a sample for measurement into the raster element after the adjustment of arrangement of the raster element and detecting the diffracted X-rays having passed through the raster element while changing the position of the raster element against the diffraction angle of the X-ray. Because of this, it is possible to disperse the influence by the honeycomb lattice caused for each diffraction angle and to make uniform the intensity variation resulting from the honeycomb lattice.

(5) Furthermore, the X-ray intensity correction method of the present invention is characterized in that the diffracted X-rays having passed through the raster element are detected by moving the raster element in synchronization with TDI scan for detecting the diffracted X-rays. Because of this, it is possible to make uniform the intensity variation resulting from the honeycomb lattice by performing the TDI scan.

(6) In addition, the X-ray intensity correction method of the present invention is characterized in that a structure for adjusting temperature is provided around the sample and the diffracted X-rays are detected in situ. Because of this, it is possible to detect only the diffracted X-rays from the sample by cutting off the scattered rays from the structure for adjusting temperature, such as a dome, by the raster element.

(7) Moreover, the X-ray intensity correction method of the present invention is characterized in that X-rays are entered onto the surface of the sample for measurement at a glazing angle and diffracted X-rays emitted at a glazing angle are detected. Because of this, it is possible to prevent reduction in resolution caused by the spread of an X-ray diffraction image in so-called glazing angle incidence X-ray diffraction measurements.

(8) Furthermore, the X-ray diffractometer of the present invention is an X-ray diffractometer for detecting diffracted X-rays by irradiating a sample with X-rays, the diffractometer characterized by including a raster element formed by polycapillaries and having a unique focal point, a detector configured to detect X-rays having passed through the raster element, and an adjusting mechanism configured to enable the adjustment of arrangement of the raster element so that the focal point of the raster element coincides with the gonio center, wherein X-rays are detected by oscillating the raster element with the detector. Because of this, it is possible to easily adjust the raster element to an optimum position and to disperse the influence of the intensity variation by the TDI scan. As a result, it is possible to make the background uniform at the time of measurement.

According to the present invention, it is possible to easily adjust the raster element to an optimum position and to make the background uniform at the time of measurement.

DETAILED DESCRIPTION OF THE INVENTION

Figure 1:
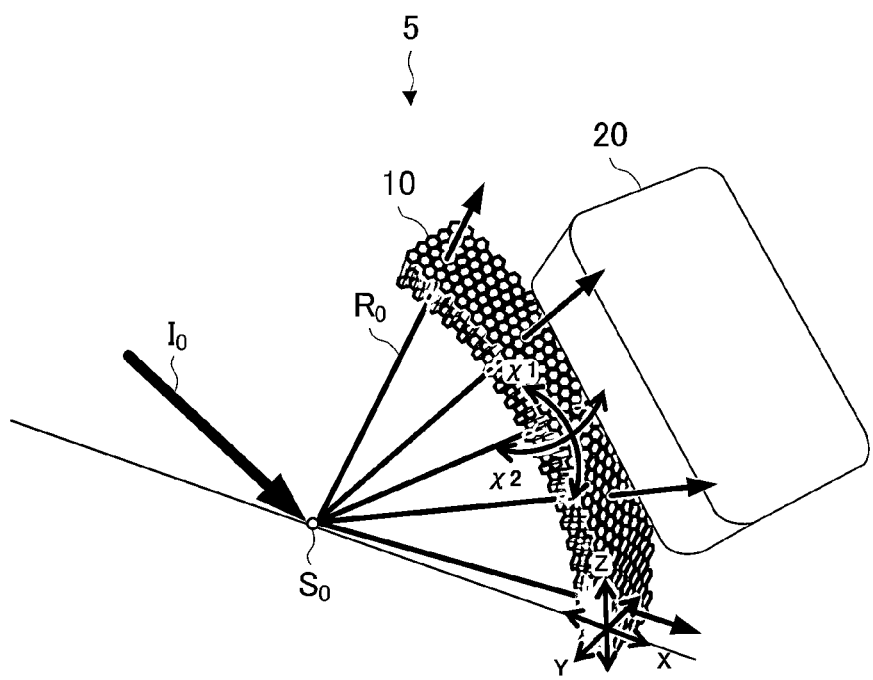
FIG. 1 is a perspective view schematically showing a configuration of an X-ray diffractometer according to the present invention.

Embodiments of the present invention are explained with reference to the drawings as follows. In order to make understanding of explanation easy, in each drawing, the same reference numeral is attached to the same component and duplicated explanations are omitted.

(Principle of X-Ray Intensity Correction Method)

Figure 2:
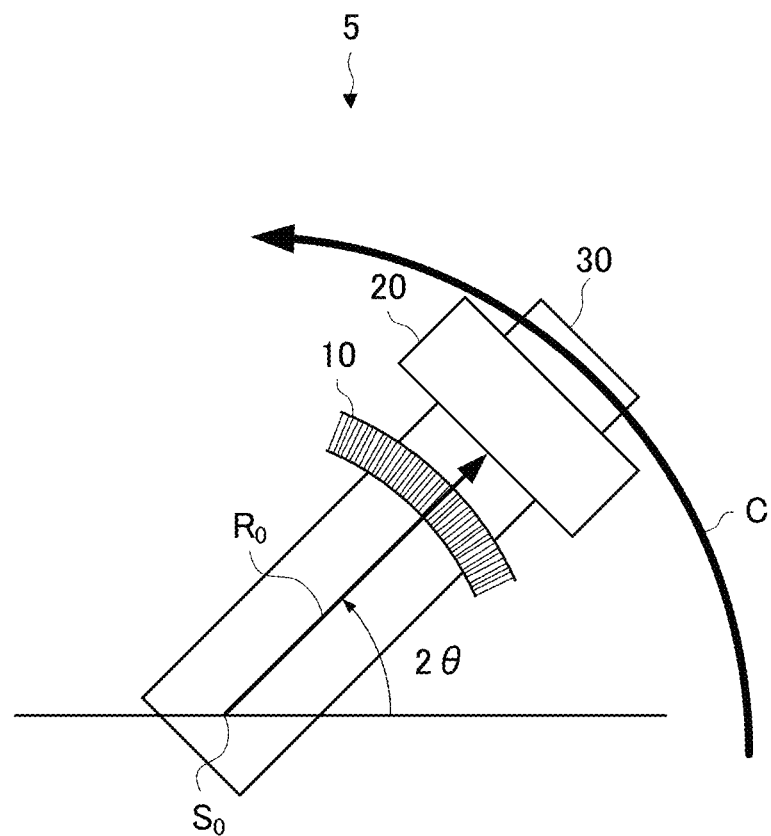
FIG. 2 is a side view schematically showing the configuration of the X-ray diffractometer according to the present invention.

FIGS. 1 and 2 are a perspective view and a side view each schematically showing a configuration of an X-ray diffractometer 5. As shown in FIGS. 1 and 2, the X-ray diffractometer 5 includes a raster element 10, a detector 20, an arm 30, and a adjusting mechanism (not shown) and X-rays diffracted by a sample are entered into the raster element 10 and diffracted X-rays $R_0$ having passed through the raster element 10 are detected. In the X-ray intensity correction method of the present invention, a sample for correction is placed at a gonio center $S_0$ and the gonio center $S_0$ is irradiated with X-rays to generate fluorescent X-rays. Then, the generated fluorescent X-rays are entered into the raster element 10 and an image of the X-rays having passed therethrough is detected, and then, the raster element 10 is adjusted based on the image so that the focal point of the raster element 10 (center of curvature) is caused to can be at the gonio center $S_0$. A sample for measurement is placed in the X-ray diffractometer 5 in which the raster element 10 is adjusted in this manner, the sample for measurement is irradiated with incidence X-rays $I_0$, and the diffracted X-rays $R_0$ are caused to pass through the raster element 10. As a result, in the intensity of the background of the diffracted X-rays $R_0$ detected, unevenness depending on angles is hard to occur.

As described above, in the X-ray intensity correction method of the present invention, the fluorescent X-rays are used, and thus, it is possible to enter the fluorescent X-rays generated uniformly on the spherical surface from the gonio center $S_0$, into the raster element 10. At this time, it is possible to adjust the position of the raster element 10 by utilizing the fact that if the focal point of the raster element 10 coincides with the gonio center $S_0$, the intensity of the detected X-rays becomes uniform regardless of the detected position. Because of this, the raster element 10 is easily adjusted to an optimum position and the background of the X-ray intensity detected at the time of measurement is made uniform.

The raster element 10 is formed by integrating polycapillaries in a planar manner. The raster element 10 is an aggregate of polycapillaries having a thickness of about 1.5 mm. A honeycomb lattice is formed by a number of polycapillaries and the whole of the raster element is worked into the shape of a sphere so as to point to a unique focal point. Further, the honeycomb lattice itself is configured by a number of polycapillaries and designed so that the axis of the hole of the polycapillary points to the focal point (in the radial direction). The raster element 10 is installed on the receiving side of the system.

Meanwhile, the polycapillary itself is formed by lead glass and the inner wall thereof is formed by a material coated with lead or other heavy elements, and X-rays incident at an angle higher than the total reflection critical angle for total reflection of the material of the inner wall are absorbed. Consequently, the raster element 10 does not allow X-rays other than components that do not hit the inner wall and pass through the capillary and components totally reflected by the inner wall, to pass through. Therefore, if the raster element 10 is not focused with respect to the gonio center, the background intensity varies depending on the detected position and the whole intensity is reduced.

It is preferable that the raster element 10 is fixed against the detector 20 and a oscillating operation of the raster element 10 is possible with the gonio center $S_0$ as a center together with the detector 20. For example, as shown in FIG. 2, by fixing the raster element 10 also on the arm 30 on which the detector 20 is fixed and by moving the arm 30, the raster element 10 and the detector 20 can be oscillated along an arc with the gonio center $S_0$ as a center by an operation. A oscillating direction C by the arm is an arc direction with the gonio center $S_0$ as a center. It should be noted that a configuration may be one in which the detector 20 is fixed and only the raster element 10 can be oscillated.

The adjusting mechanism enables the adjustment of arrangement of the raster element 10. The adjusting mechanism is configured by, for example, two kinds of knob and a transmitting mechanism transmitting the movement thereof to the raster element 10. The two kinds of knob include one controlling translation movement (X, Y, Z) and one controlling tilting movement ($\chi 1$, $\chi 2$). By using this adjusting mechanism, the installation position is adjusted in advance so that the focal point of the raster element 10 coincides with the gonio center $S_0$. At this time the distance from the gonio center $S_0$ to the raster element 10 coincides with the radius of curvature of the raster element 10.

The detector 20 is a two-dimensional detector and detects X-rays having passed through the raster element 10. A two-dimensional detector has the position resolution of its own, and thus a narrow slit for causing the detector to have the position resolution is not set in front of the detector and is used as an open detector. As described above, the detector 20 is an open detector, and thus detects not only the diffracted component from the sample but also scattered X-rays from therearound and as a result, also obtains different information. Because of this, by providing the raster element 10 and by the detector 20 detecting diffracted X-rays having passed through the raster element 10, it is made possible to detect only the diffracted X-rays generated from the gonio center $S_0$.

Such a detection can be performed effectively by adjustment of the position of the focal point of the raster element 10.

It is preferable that the detector 20 is a detector capable of TDI (Time Delay Integration) scan and when oscillating of the detector 20 is accompanied, a configuration for the TDI scan is required. For example, the TDI scan is enabled by fixing the detector 20 on the arm 30 as shown in FIG. 2 and by oscillating the detector 20 together with the raster element 10 fixed on the arm 30. By oscillating the raster element 10 in synchronization with the TDI scan of the detector 20, it is possible to make uniform the intensity variation by lessening the influence of the honeycomb lattice on the detected image.

Meanwhile, in the example shown in FIG. 2, the raster element 10 and the detector 20 are fixed on the arm 30, but the oscillating by the arm 30 is not necessarily required. It may also be possible to perform detecting by fixing the detector 20 against the gonio center $S_0$ and oscillating the raster element 10 or to perform detecting by fixing the raster element 10 and oscillating the detector 20.

EXAMPLE 1

An X-ray intensity correction method that can be performed by using the above-mentioned X-ray diffractometer 5 is explained as follows. First, a sample for correction is placed at the gonio center $S_0$. As for the sample for correction, there is included, for example, $Fe_3O_4$ powder, which is a sample that generates fluorescent X-rays, in a ordinary diffractometer using a Cu target. Such an iron-based substance is preferable for the sample for correction. Next, X-rays are focused on the gonio center $S_0$ and the fluorescent X-rays excited by the focused X-rays are entered into the raster element 10 having a unique focal point and the fluorescent X-rays having passed through the raster element 10 are detected. At the time of adjustment, X-ray beams focused on a point at the gonio center are used and the intensity of the fluorescent X-rays excited by the X-rays is monitored by the detector 20.

Then, the arrangement of the raster element is adjusted so that the detected fluorescent X-rays are uniform regardless of the detected position. That is, the position (mainly translation X, Y, Z, tilting $\chi 1$, $\chi 2$) of the raster element 10 is moved and adjusted to an optimum position while performing monitoring so that the fluorescent X-rays pass through the whole of the raster element 10 uniformly. Being uniform is determined by the fact that the minimum value of the intensity within the monitored two-dimensional image reaches or exceeds half the maximum value of the intensity. Because of this, it is possible to sufficiently adjust the arrangement of the raster element and to make the background uniform at the time of measurement. Meanwhile, it is further preferable that the intensity in each position is within ±20% of the average intensity.

It should be noted that the adjustment of arrangement of the raster element 10 is performed, as described above, by moving the raster element 10, in the translation direction and in the tilting direction in accordance with the intensity distribution of the image of the fluorescent X-rays having passed through the raster element 10. Specifically, by viewing the two-dimensional image of the fluorescent X-rays, for example, if the intensity at the center part of the two-dimensional image is relatively high, the intensity at the center part of the two-dimensional image is reduced and the intensity on the periphery is increased and the method etc. for moving the translation axis X so that the intensity becomes uniform as a whole is performed. Because of this, it is known in which direction the movement of translation or tilting is necessary in accordance with the pattern of the intensity distribution, and thus it is possible to efficiently adjust the arrangement of the raster element. In this manner, it is possible to correct the intensity of diffracted X-rays detected by making the background uniform. Meanwhile, it may also be possible to perform the adjustment of arrangement of the raster element while detecting the two-dimensional image of the fluorescent X-rays or to alternately perform the detection of the two-dimensional image and the arrangement adjustment based on the two-dimensional image.

(Experiment 1)

The above-mentioned X-ray intensity correction method was performed and the intensity of the background is corrected. As the raster element 10, a raster element having a thickness of about 1.5 mm was used. As the sample for correction, $Fe_3O_4$ powder was used and as the sample for measurement, $Al_2O_3$ powder was used. As the detector 20, a detector capable of the TDI scan was used and at the time of arrangement adjustment of the raster element 10, the fluorescent X-rays were detected with the arm 30 fixed and at the time of detection of diffracted X-rays, the TDI scan was performed by oscillating the raster element 10 and the detector 20 by the arm 30.

Figure 3:
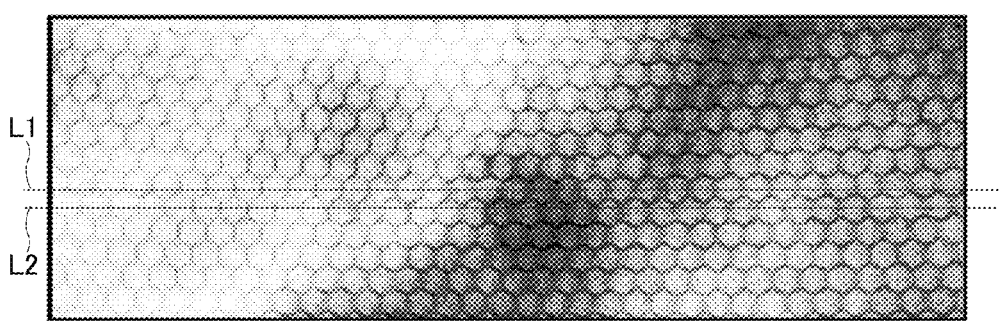
FIG. 3 is a image showing a result of the fluorescent X-ray intensity before adjustment of a raster element.
Figure 4:
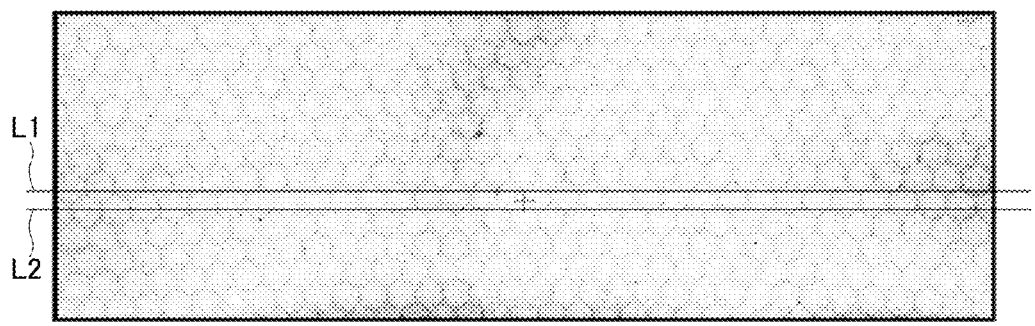
FIG. 4 is a image showing a result of the fluorescent X-ray intensity after adjustment of the raster element.
Figure 5:
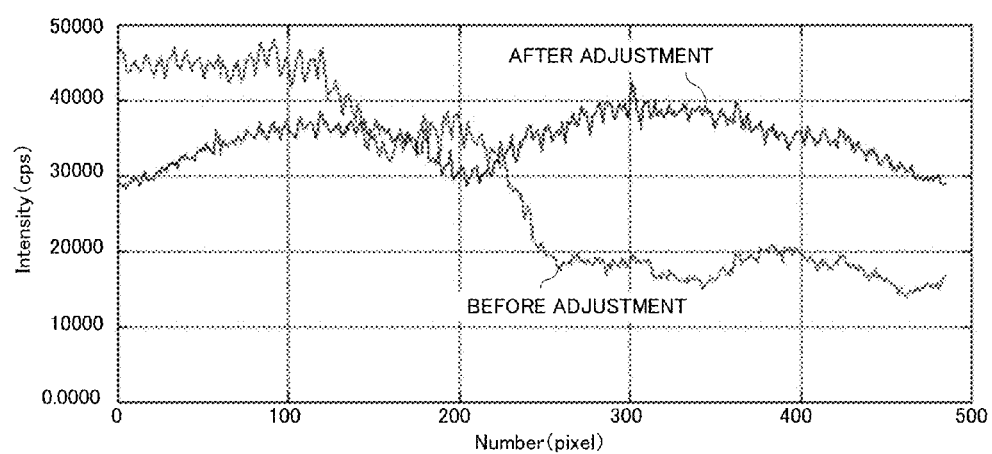
FIG. 5 is a graph showing a result of plotting intensities along cut-out lines between L1 and L2 for pixels in a 2θ direction.

FIGS. 3 and 4 are images showing the fluorescent X-ray intensity distribution before and after the adjustment of the raster element 10, respectively. FIG. 5 is a graph showing the result of plotting the intensities at the cut-out lines between L1 and L2 shown in FIGS. 3 and 4 for the pixels in the horizontal direction. It is possible to sufficiently adjust the arrangement of the raster element 10 and to cause the focal position thereof to be at the gonio center by referring to the fluorescent X-ray monitoring results as shown in FIGS. 3 and 4 and by repeating the adjustment of the raster element 10 so that the intensity as a whole falls within a reference and becomes uniform as shown in FIG. 5. As the above-mentioned reference, it is possible to adopt the condition as a reference that the minimum value of the intensity within the two-dimensional image obtained by the detected fluorescent X-rays reaches or exceeds half the maximum value of the intensity within the two-dimensional image. In the plot before adjustment shown in FIG. 5, the maximum value is about 49,000 cps while the minimum value is about 16,000 cps, and thus, the minimum value is less than half the maximum value. In the plot after adjustment, the maximum value is about 42,000 cps while the minimum value is about 29,000 cps, and thus the minimum value is equal to or more than half the maximum value.

Figure 6:
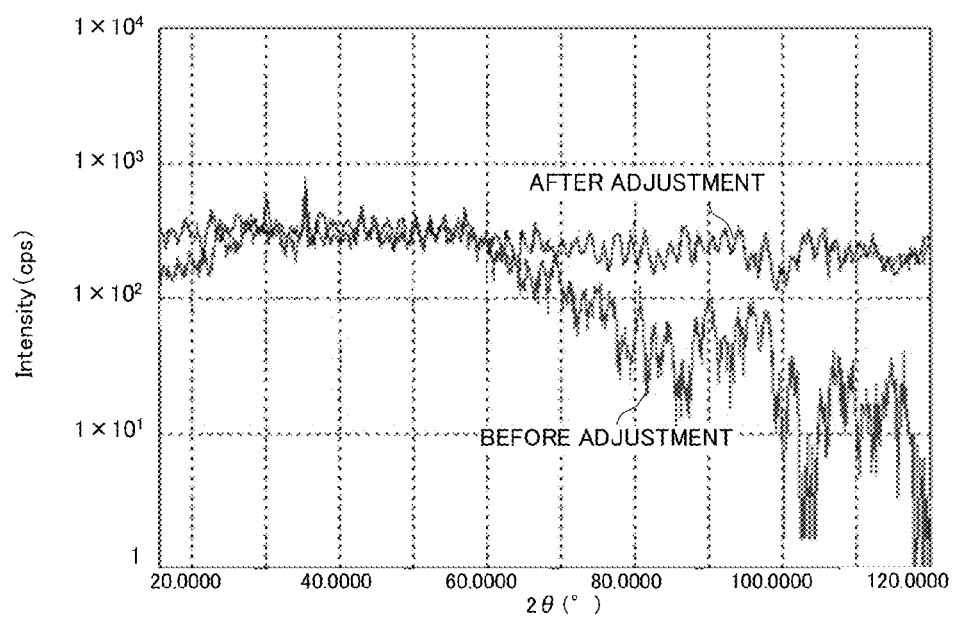
FIG. 6 is a graph showing each of the intensities of the background before and after adjustment of the raster element.

In addition, FIG. 6 is a graph showing the intensities of the fluorescent X-rays before and after adjustment of the raster element 10, respectively. As shown in FIG. 6, the detected intensity before the raster element adjustment is reduced on the side of higher angles in comparison with that on the side of lower angles, exhibiting a wavy shape. In contrast to this, the detected intensity after the raster element adjustment is equal on the side of lower angles and on the side of higher angles, forming a flat shape. As described above, it is possible to easily make the background uniform by the above-mentioned adjustment of the raster element 10.

The raster element 10 itself, however, forms a number of honeycomb lattices, and thus, even by the above-mentioned adjustment, the X-rays do not pass through the boundary of honeycomb lattices and the intensity becomes non-uniform. The intensity variation of the curve after adjustment shown in FIG. 6 is flat when viewed in a wide range, but in a narrow range, small fluctuations are detected. The reason is that there is a difference in magnitude of the intensity between the inside and the boundary of the honeycomb lattice. In such a case, it is possible to make uniform the small intensity variation by further performing intensity correction of diffracted X-rays.

EXAMPLE 2

Figure 7:
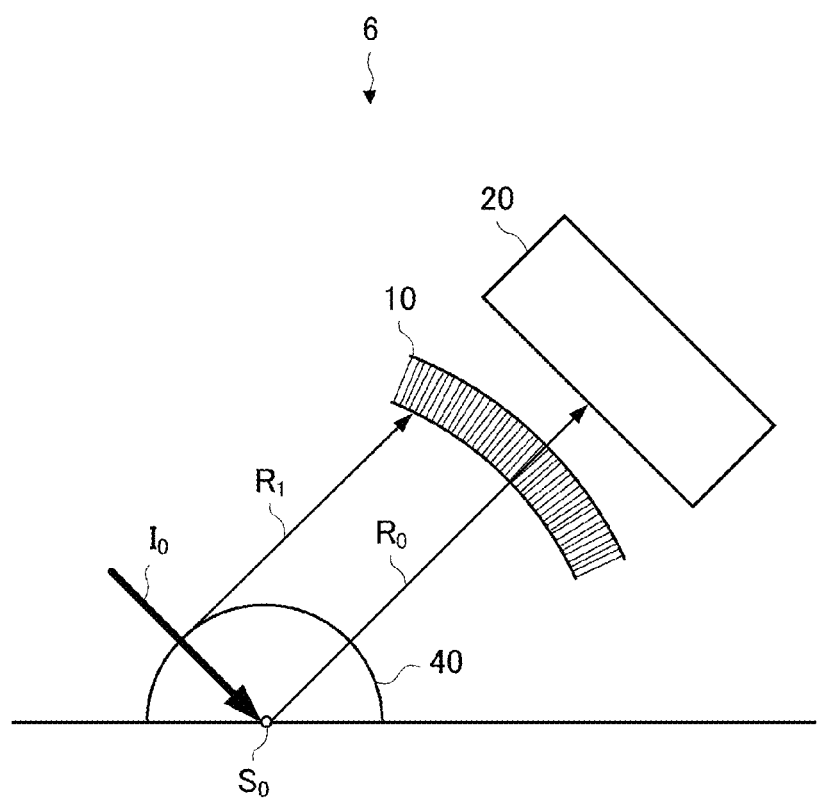
FIG. 7 is a side view showing a configuration when performing measurements using a structure for adjusting temperature (Example).

As an example of the above-mentioned method, a case where a structure for adjusting temperature is provided around a sample and diffracted X-rays are detected in situ is explained while comparing the example with a comparative example. FIG. 7 is a side view showing a configuration when performing measurements using the structure for adjusting temperature. An X-ray diffractometer 6 shown in FIG. 7 has a dome 40 as the high-temperature attachment (manufactured by Anton Peer), which is a structure for maintaining a temperature. In this case, it is possible to maintain high temperature of a sample by a heater under the sample within the dome 40 and it becomes possible to perform measurements in situ. At this time, as the detector 20, a two-dimensional detector can be used, but it may also be possible to use a one-directional detector. At this time, the one-dimensional or two-dimensional detector is an open detector, and thus scattered rays other than those from the sample are detected.

Consequently, in the example, in order to detect diffracted rays only from the sample, the configuration of the X-ray diffractometer 6 is adopted, in which the raster element 10 is installed on the receiving side. Because of this, it is possible to shut off diffracted rays and scattered rays $R_1$ from the dome 40, by the raster element 10. If, however, data is acquired with the raster element 10 and the detector 20 fixed, intensity variation is caused resulting from the honeycomb lattice of the raster element 10. In order to solve the problem of intensity variation, the intensity is made uniform by oscillating the raster element and the detector at the same time (TDI scan).

(Experiment 2-1)

Figure 8:
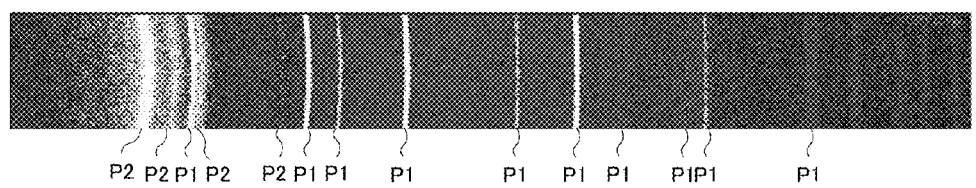
FIG. 8 is a diffraction image obtained by using the structure for adjusting temperature without the raster element (Comparative Example).
Figure 9:
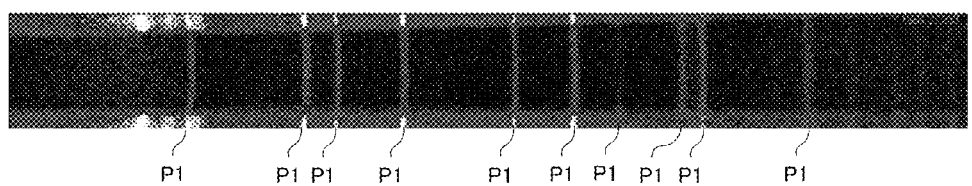
FIG. 9 is a diffraction image obtained by using the structure for adjusting temperature with the raster element provided (Example).
Figure 10:
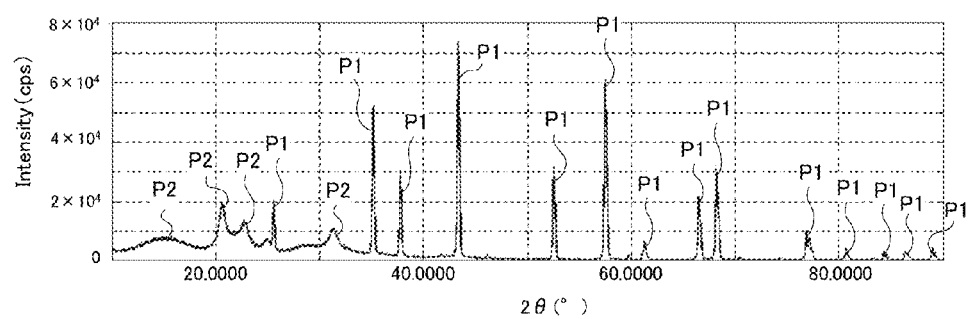
FIG. 10 is an X-ray intensity profile obtained by using the structure for adjusting temperature without the raster element (Comparative Example).
Figure 11:
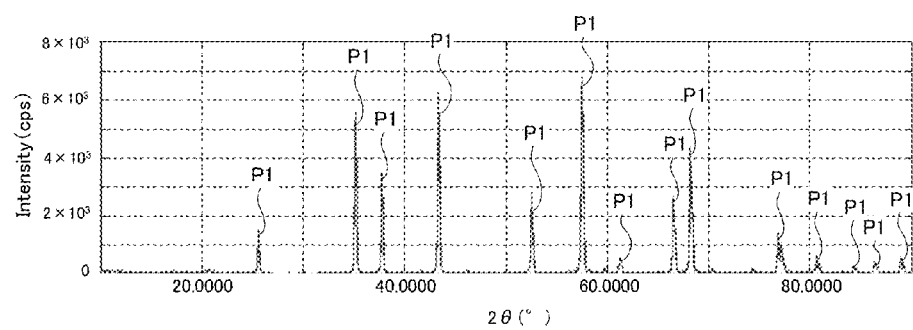
FIG. 11 is an X-ray intensity profile obtained by using the structure for adjusting temperature with the raster element provided (Example).

As the sample, $Al_2O_3$ powder was used. The sample was covered with the attachment of the dome of the high-temperature attachment and diffracted X-rays were detected when the raster element 10 was and was not installed. FIG. 8 is a diffraction image (comparative example) obtained without the raster element 10 and FIG. 9 is a diffraction image (example) obtained with the raster element 10 provided. Furthermore, FIG. 10 is an X-ray intensity profile (comparative example) obtained without the raster element 10 and FIG. 11 is an X-ray intensity profile (example) obtained with the raster element 10 provided. FIGS. 10 and 11 are profiles obtained by converting the two-dimensional images of FIGS. 8 and 9 into one-dimensional data, respectively.

As shown in FIG. 8, when the raster element 10 is not installed, a number of diffracted rays P2 by PEEK (polyether ether ketone) of the material of the dome of the high-temperature attachment are detected, but when the raster element 10 is installed, the diffracted rays P2 of PEEK are removed and only diffracted rays P1 of the $Al_2O_3$ powder of the sample are detected. As described above, it was possible to completely remove the diffracted rays P2 from the dome 40 when the raster element 10 was installed.

(Experiment 2-2)

Figure 12:
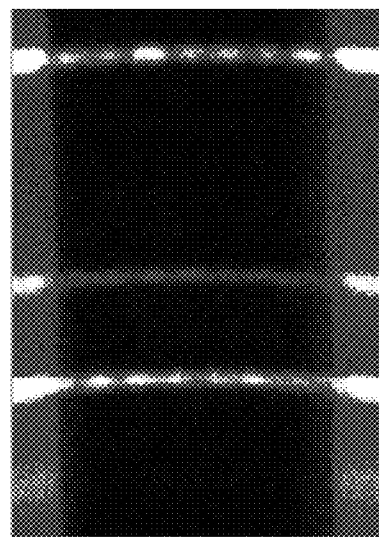
FIG. 12 is a diffraction image obtained by fixing the raster element and a detector (Comparative Example).
Figure 13:
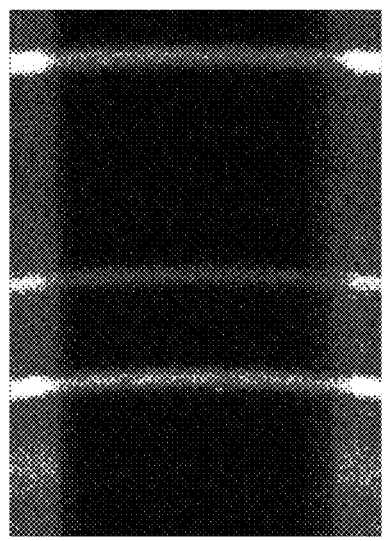
FIG. 13 is a diffraction image obtained by oscillating the raster element and the detector (Example).

Furthermore, diffraction images when the arm 30 was fixed and the arm 30 was oscillated were detected respectively by using the X-ray diffractometer 6 in which the raster element 10 and the detector 20 are fixed on the arm 30. FIG. 12 is a diffraction image obtained by fixing the raster element 10 and the detector 20 and FIG. 13 is a diffraction image obtained by oscillating the raster element 10 and the detector 20. It has been found that when the raster element 10 and the detector are fixed, the intensity variation caused by the honeycomb lattice of the raster element 10 can be observed as shown in FIG. 12, but the intensity variation is made uniform by oscillating as shown in FIG. 13.

EXAMPLE 3

Figure 14:
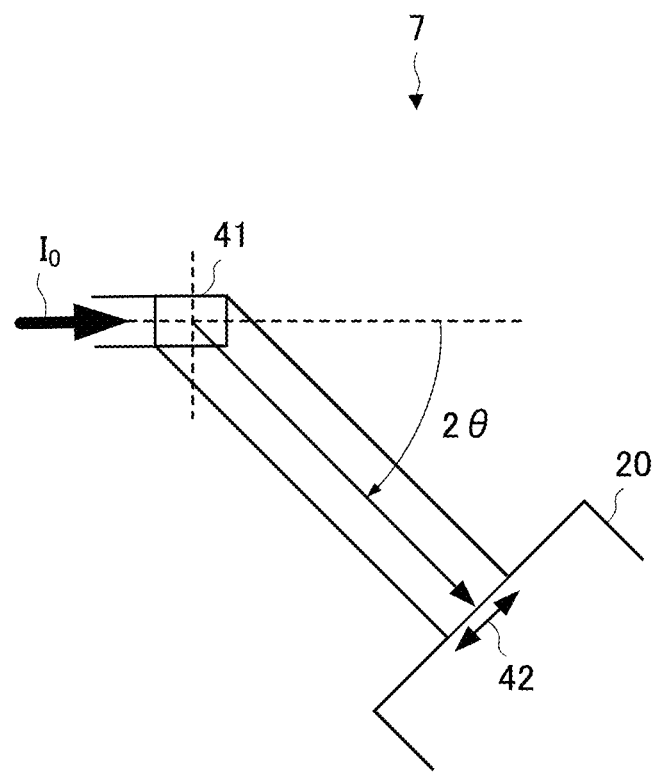
FIG. 14 is a plan view showing a configuration for performing glazing angle incidence X-ray diffraction measurements without the raster element (Comparative Example).
Figure 15:
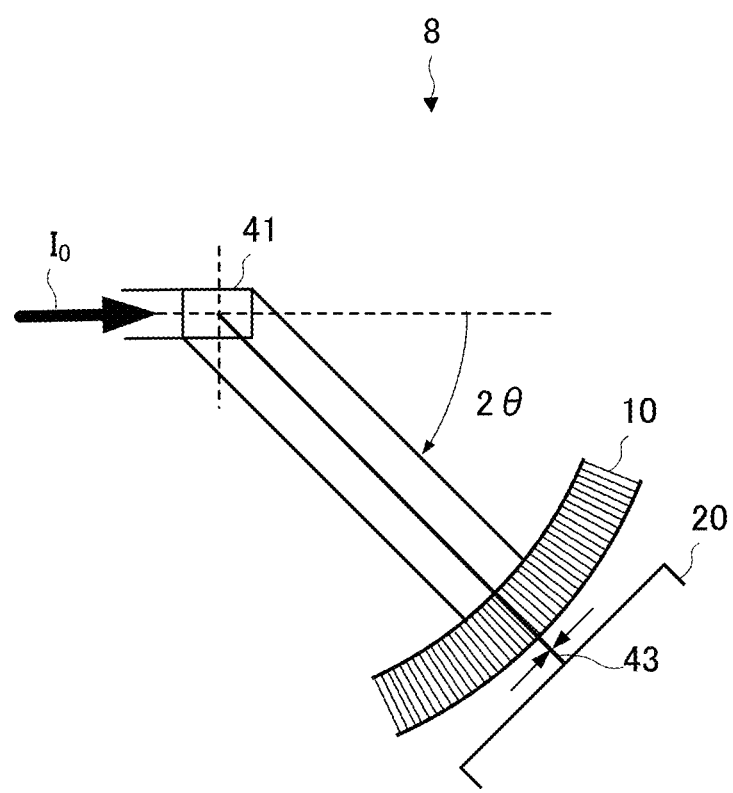
FIG. 15 is a plan view showing a configuration for performing glazing angle incidence X-ray measurements with the raster element provided (Example).

As another example, a case where X-rays are entered onto the surface of a sample at a glazing angle and the diffracted X-rays emitted at a glazing angle are detected is explained while comparing the example with a comparative example. FIG. 14 is a plan view showing a configuration when glazing angle incidence X-ray diffraction measurements are performed without the raster element 10 (comparative example) and FIG. 15 is a plan view showing a configuration when glazing angle incidence X-ray diffraction measurements are performed with the raster element 10 provided (example).

In the example of glazing angle incidence, a two-dimensional detector is used as the detector 20. As shown in FIG. 14, when X-rays incident at a glazing angle are detected by a two-dimensional detector as in glazing angle incidence X-ray diffraction measurements with an X-ray diffractometer 7 not having the raster element, usually, a spread 42 of a two-dimensional image of acquired diffracted components is caused by a spread 41 of X-rays at the position of a sample and resolution is deteriorated. That is, the two-dimensional image is elongated in the transverse direction by the influence of glazing angle incidence. In contrast to this, with an X-ray diffractometer 8 in which the raster element 10 is installed shown in FIG. 15, it is possible to prevent the spread 42 of the diffraction image by detecting diffracted X-rays 43 having passed through the raster element 10, and thus resolution can be improved.

In this case also, however, if data is acquired with the raster element 10 and the detector 20 being fixed, the intensity variation resulting from the honeycomb lattice of the raster element 10 is caused. In order to solve the problem of the intensity variation, in the present example, the intensity is made uniform by oscillating the detector and the raster at the same time (TDI scan) or oscillating only the raster.

(Experiment 3)

Figure 16:
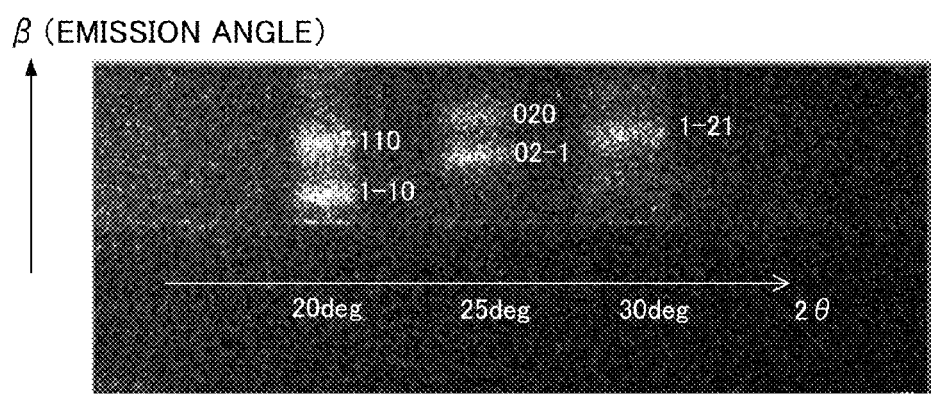
FIG. 16 is a diffraction image when performing glazing angle incidence X-ray diffraction measurements without the raster element (Comparative Example).

First, glazing angle incidence X-ray diffraction was measured by utilizing a two-dimensional detector without the raster element 10. FIG. 16 is a diffraction image when glazing angle incidence X-ray diffraction measurements are performed without the raster element (comparative example). The numerical values in FIG. 16 indicate indexes of lattice planes. In the glazing angle incidence X-ray diffraction measurements, the incidence angle of the X-ray on the sample is very low, that is, 1 degree or less, and thus the irradiation width of X-ray increases on the sample. When the glazing angle incidence X-ray diffraction is measured by a two-dimensional detector in this state, the effect of the increase in the irradiation width is reflected in the detector as it is and an X-ray diffraction image is an image spread in proportion to the irradiation width.

Figure 17:
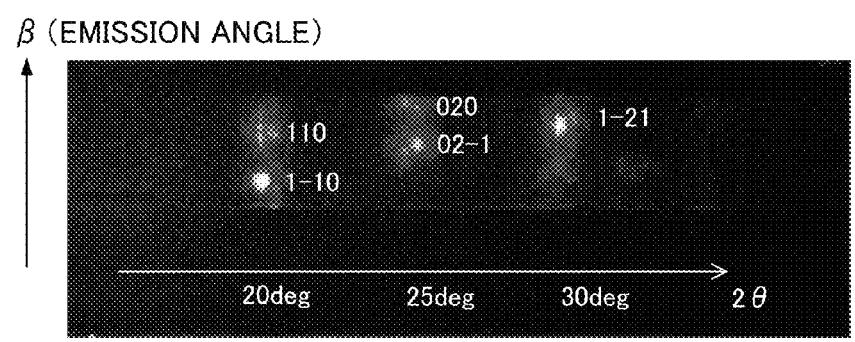
FIG. 17 is a diffraction image when performing glazing angle incidence X-ray diffraction measurements with the raster element provided (Example).
Figure 18:
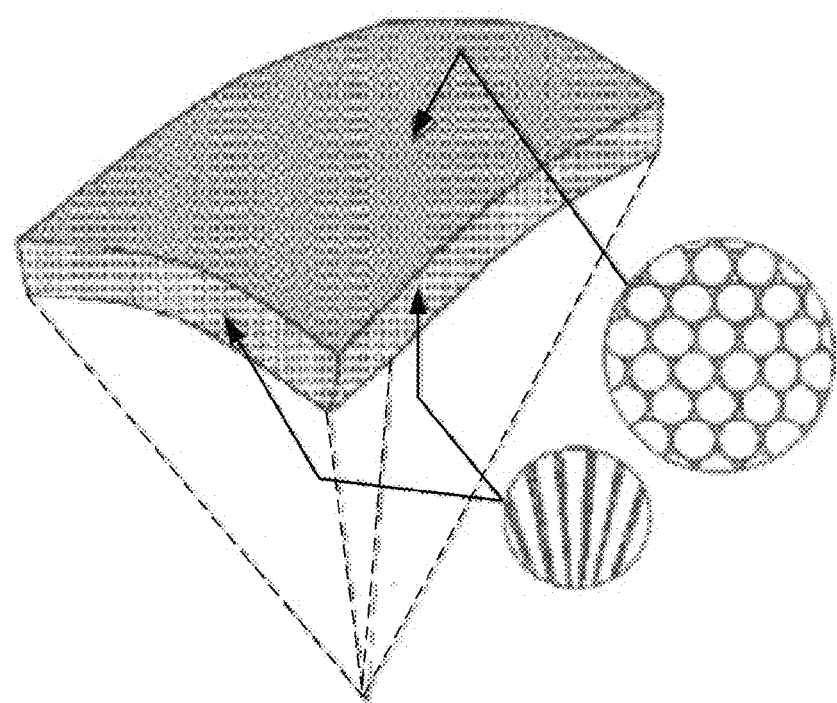
FIG. 18 is a perspective view showing a configuration of a general raster element.
Figure 19:
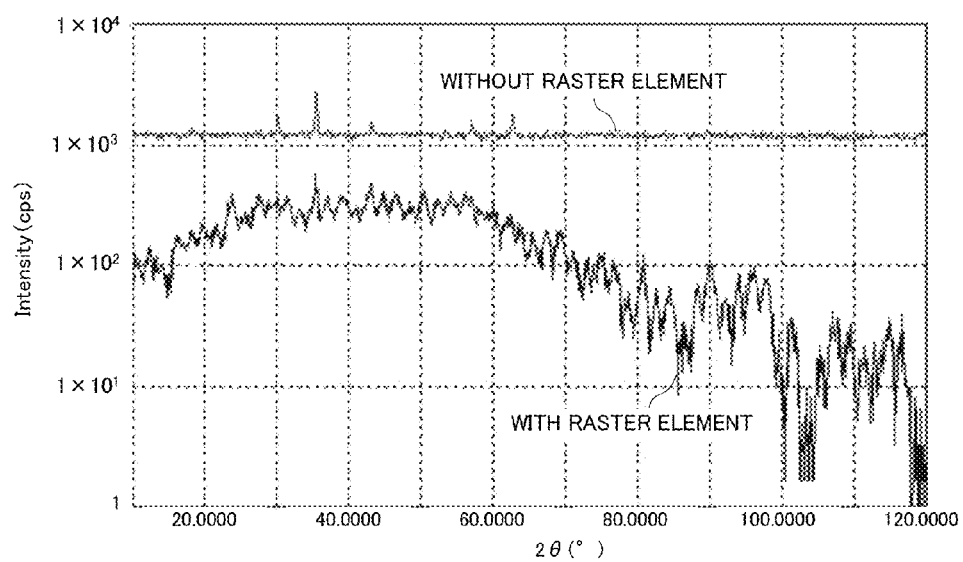
FIG. 19 is a graph showing the intensities of the background by a detection method with and without the raster element, respectively.

In contrast to this, measurements were performed with the raster element introduced in front of the two-dimensional detector. FIG. 17 is a diffraction image when the raster element is provided and the glazing angle incidence X-ray diffraction measurements are performed (example). Numerical values in FIG. 17 indicate indexes of lattice planes. It has been found that because of the features of only diffracted rays in the vicinity of the gonio center being able to pass through the element, the diffraction image is observed in the form of a spot in comparison with the state where no raster element is provided and as a result, the resolution of the glazing angle incidence X-ray diffraction measurements is improved.

What is claimed is:

1. An X-ray intensity correction method for correcting an intensity of diffracted X-rays by making a background uniform, the method comprising:
   focusing X-rays on a sample for correction placed at a gonio center to produce fluorescent X-rays, entering the fluorescent X-rays excited by the X-rays into a raster element being formed by polycapillaries and having a unique focal point, and detecting the fluorescent X-rays having passed through the raster element; and
   adjusting an arrangement of the raster element so that the fluorescent X-rays can uniformly be detected regardless of a detecting position, wherein
   the arrangement of the raster element is adjusted to a position determined based on a comparison between a minimum value and a maximum value of an intensity of a two-dimensional image obtained by the fluorescent X-rays.

2. An X-ray intensity correction method for correcting an intensity of diffracted X-rays by making a background uniform, the method comprising:
   focusing X-rays on a sample for correction placed at a gonio center to produce fluorescent X-rays, entering the fluorescent X-rays excited by the X-rays into a raster element being formed by polycapillaries and having a unique focal point, and detecting the fluorescent X-rays having passed through the raster element; and
   adjusting an arrangement of the raster element so that the fluorescent X-rays can uniformly be detected regardless of a detecting position, wherein
   the arrangement of the raster element is adjusted until a minimum value become half or more of a maximum value of an intensity of a two-dimensional image obtained by the fluorescent X-rays.

3. The X-ray intensity correction method according to claim 1, wherein
   the arrangement of the raster element is adjusted by moving the raster element in a translation direction and in a tilting direction in accordance with an intensity distribution of the two-dimensional image of the fluorescent X-rays having passed through the raster element.

4. The X-ray intensity correction method according to claim 1, further comprising:
   entering the X-rays diffracted by a sample for measurement into the raster element after the adjustment of arrangement of the raster element and detecting the diffracted X-rays having passed through the raster element while changing the position of the raster element against the diffraction angle of the X-rays.

5. The X-ray intensity correction method according to claim 4, wherein
   the diffracted X-rays having passed through the raster element are detected by moving the raster element in synchronization with TDI scan for detecting the diffracted X-rays.

6. The X-ray intensity correction method according to claim 1, wherein
   a structure for adjusting temperature is provided around the sample and the diffracted X-rays are detected in situ.

7. The X-ray intensity correction method according to claim 1, wherein
   X-rays are entered onto a surface of the sample for measurement at a glazing angle and diffracted X-rays emitted at a glazing angle are detected.

8. An X-ray diffractometer for detecting diffracted X-rays by irradiating a sample with X-rays, the diffractometer comprising:

a raster element formed by polycapillaries and having a unique focal point;

a detector configured to detect X-rays having passed through the raster element; and an adjusting mechanism configured to enable an adjustment of arrangement of the raster element so that a focal point of the raster element can be set at a gonio center, wherein the X-rays are detected by oscillating the raster element with the detector, the raster element is provided to be adjustable independently from the detector with the adjusting mechanism, the adjustment of the arrangement of the raster element is prepared to focus X-rays on a sample for correction placed at a gonio center to produce fluorescent X-rays, entering the fluorescent X-rays excited by the focused X-rays into the raster element, and detecting the fluorescent X-rays having passed through the raster element, and the arrangement of the raster element is adjusted to a position determined based on a comparison between a minimum value and a maximum value of an intensity of a two-dimensional image obtained by the fluorescent X-rays.

9. The X-ray intensity correction method according to claim 1, wherein the arrangement of the raster element is adjusted to a position in case where the minimum value become half or more of the maximum value on the intensity in the two-dimensional image obtained by fluorescent X-rays.

10. The X-ray diffractometer according to claim 8, wherein the arrangement of the raster element is adjusted to a position in case where the minimum value become half or more of the maximum value on the intensity in the two-dimensional image obtained by fluorescent X-rays.

* * * * *